United States Patent [19]
Asaka et al.

[11] Patent Number: 5,804,565
[45] Date of Patent: Sep. 8, 1998

[54] ERYTHROMYCIN A DERIVATIVES

[75] Inventors: Toshifumi Asaka, Konosu; Tetsuya Tanikawa, Fuchu; Takaaki Ishii, Urawa; Masato Kashimura, Omiya, all of Japan

[73] Assignee: Taisho Pharmaceutical Co., Ltd., Tokyo, Japan

[21] Appl. No.: 931,949

[22] Filed: Sep. 17, 1997

[30] Foreign Application Priority Data

Sep. 24, 1996 [JP] Japan ................... 8-251050

[51] Int. Cl.⁶ .................. C07H 17/08; A01N 9/00
[52] U.S. Cl. .................. 514/29; 536/7.2; 536/7.4
[58] Field of Search ............. 536/7.2, 7.4; 514/29

[56] References Cited

U.S. PATENT DOCUMENTS

| | | | |
|---|---|---|---|
| 4,331,803 | 5/1982 | Watanabe et al. | 536/7.2 |
| 4,975,370 | 12/1990 | Sasaki et al. | 435/76 |
| 4,990,602 | 2/1991 | Morimoto et al. | 536/7.4 |
| 5,403,923 | 4/1995 | Kashimura et al. | 536/7.4 |
| 5,444,051 | 8/1995 | Agouridas et al. | 514/29 |
| 5,561,118 | 10/1996 | Agouridas et al. | 514/29 |

FOREIGN PATENT DOCUMENTS

| | | |
|---|---|---|
| 0487411A1 | 5/1992 | European Pat. Off. . |
| 0619319A1 | 10/1994 | European Pat. Off. . |
| 0619320A1 | 10/1994 | European Pat. Off. . |
| 2692579 | 12/1993 | France . |
| WO9501794 | 1/1995 | WIPO . |

OTHER PUBLICATIONS

The Journal of Antibiotics by G. Michael Bright et al, vol. XLI, No. 8, pp. 1029–1047, (1988).

*Primary Examiner*—Mukund J. Shah
*Assistant Examiner*—Bruck Kifle
*Attorney, Agent, or Firm*—Sughrue, Mion, Zinn, Macpeak & Seas, PLLC

[57] ABSTRACT

An erythromycin A derivative represented by the formula (I):

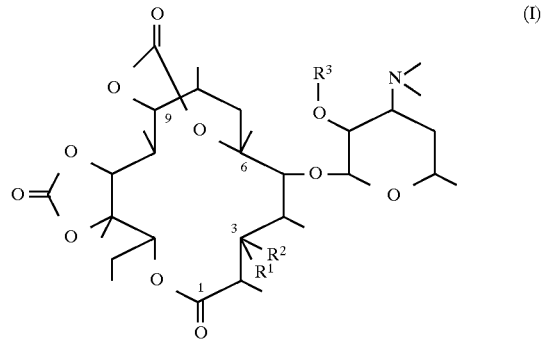

[wherein $R^1$ is a group represented by the formula: —OCOCH$_2$Y (wherein Y is a pyridyl group, a quinolyl group, a p-nitrophenyl group or a group represented by the formula: —NR$^4$R$^5$ (wherein $R^4$ and $R^5$ may be the same or different, and are each a hydrogen atom, a methyl group, a pyridylmethyl, a quinolylmethyl group or a benzyloxycarbonyl group)) or a cladinosyloxy group, $R^2$ is a hydrogen atom, or $R^1$ and $R^2$ together form an oxo group, $R^3$ is a hydrogen atom, an acetyl group, an ethylsuccinyl group or a nicotinoyl group] or a pharmaceutically acceptable salt thereof has a strong antibacterial activity against not only Gram-positive bacteria but also some Gram-negative bacteria, in particular, *Haemophilus influenzae* which is a serious factor of infectious diseases in the respiratory organs.

4 Claims, No Drawings

ERYTHROMYCIN A DERIVATIVES

TECHNICAL FIELD

The present invention relates to novel derivatives of antibiotic erythromycin A.

BACKGROUND ART

Erythromycin A is an antibiotic clinically widely used as an agent for treating infectious diseases caused by Gram-positive bacteria, mycoplasmas, etc. However, erythromycin A is decomposed by the gastric acid due to instability to acids, whereby have a drawback of no constancy of the distribution in the body. Hitherto many erythromycin A derivatives have been prepared for the improvement of the biological or pharmacological properties. For example, it is reported that 6-O-methylerythromycin A derivatives (the specification of U.S. Pat. No. 4,331,803) and 15-membered ring macrolides derived from erythromycin A [The Journal of Antibiotics, vol. 41, No. 8, 1029 (1988)] have an improved stability to acids and a superior in vivo antibacterial activity in comparison with erythromycin A when administered orally.

An object of the present invention is to provide a novel antibiotic erythromycin A derivative of the following Formula (I) or a pharmaceutically acceptable salt having a strong antibacterial activity against not only Gram-positive bacteria but also some Gram-negative bacteria, in particular, *Haemophilus influenzae* which is a serious factor of infectious diseases in the respiratory organs, and a pharmaceutical composition comprising the same as an effective component.

Other objects of the present invention are to provide a method for the treatment of a bacterially infectious disease which comprises administering a pharmaceutically effective amount of the erythromycin A derivative of Formula (I) or a pharmaceutically acceptable salt thereof to patients, and use of the erythromycin A derivative of Formula (I) or a pharmaceutically acceptable salt thereof for the treatment of a bacterially infectious disease.

DISCLOSURE OF THE INVENTION

As a result of various researches on the antibacterial activity of erythromycin A derivatives, the present inventors have found that the compounds wherein cyclic carbonate groups are introduced at the 6, 9-positions and the 11, 12-positions have a very strong antibacterial activity against not only Gram-positive bacteria but also Gram-negative bacteria, in particular, *Haemophilus influenzae*, whereby the present invention has been accomplished.

The present invention relates to an erythromycin A derivative represented by the formula (I):

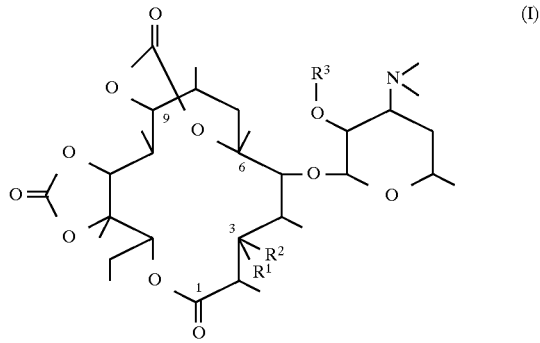

[wherein $R^1$ is a group represented by the formula: —OCOCH$_2$Y (wherein Y is a pyridyl group, a quinolyl group, a p-nitrophenyl group or a group represented by the formula: —NR$^4$R$^5$ (wherein R$^4$ and R$^5$ may be the same or different, and are each a hydrogen atom, a methyl group, a pyridylmethyl group, a quinolylmethyl group or a benzyloxycarbonyl group)) or a cladinosyloxy group, $R^2$ is a hydrogen atom, or $R^1$ and $R^2$ together form an oxo group, $R^3$ is a hydrogen atom, an acetyl group, an ethylsuccinyl group or a nicotinoyl group] or a pharmaceutically acceptable salt thereof.

In Formula (I), preferably, $R^1$ is a pyridylacetyloxy group, and $R^3$ is a hydrogen atom.

In the present invention, the pharmaceutically acceptable salt refers to a salt used in chemotherapy or prophylaxis of bacterially infectious diseases, for example, a salt with acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid, laurylsulfuric acid, malic acid, aspartic acid, glutaminic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, polyacrylate or carboxyvinyl polymer.

The compounds of the present invention can be prepared from erythromycin A 11,12-cyclic carbonate or 9-dihydroerythromycin A according to the following methods.

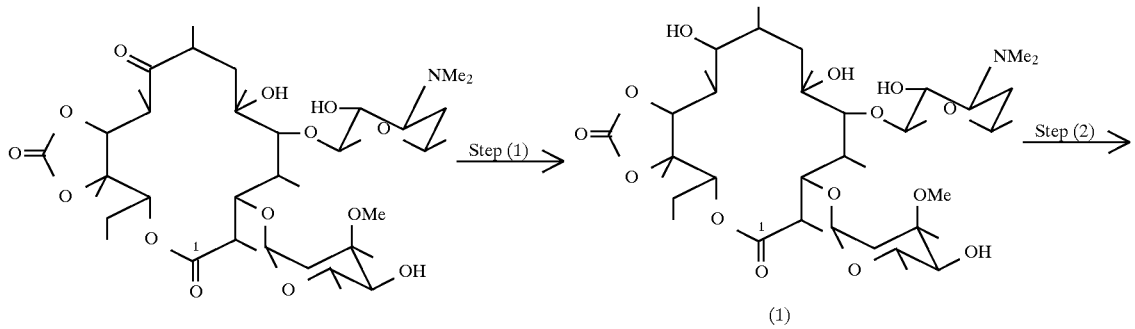

(1)

-continued
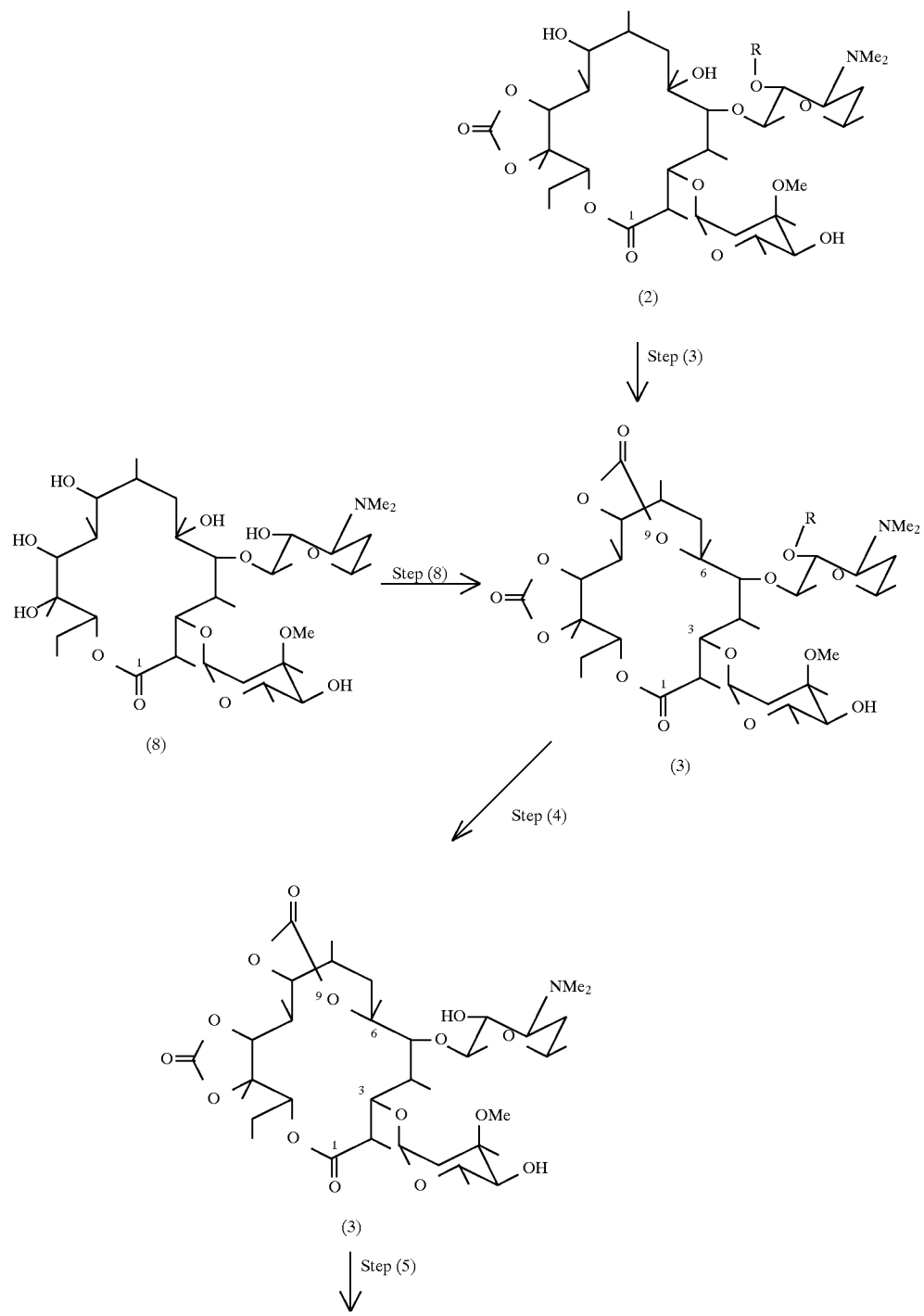

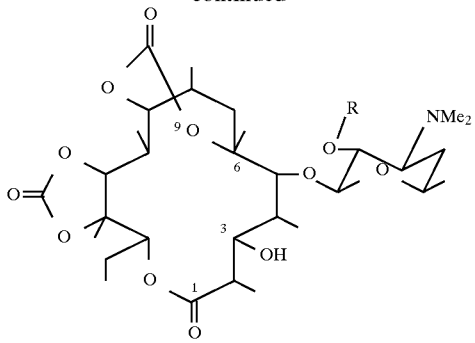

(5)

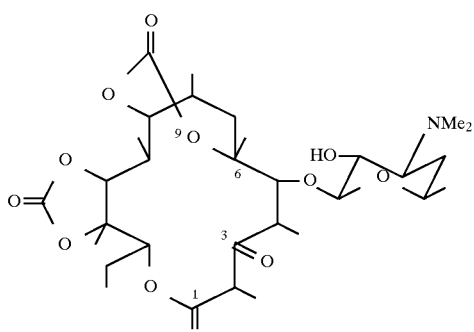

(7)

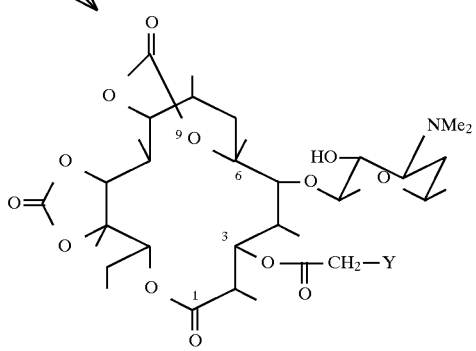

(6)

Step (1); Erythromycin A 11,12-cyclic carbonate is reacted with a reductant in a lower alcohol at a temperature of from 0° C. to 30° C. to give Compound (1). Examples of the lower alcohol to be used herein are methanol, ethanol, propyl alcohol and butyl alcohol. Preferable examples of the reductant to be used are sodium borohydride and sodium cyanoborohydride.

Step (2); Compound (1) is reacted in an inert solvent with an acid anhydride represented by the formula: $R^2O$ (wherein R is an acetyl group, an ethylsuccinyl group, a nicotinoyl group or a benzoyl group) or a halide represented by the formula: R—X (wherein R is as defined above, X is a halogen atom), if necessary, in the presence of a base at a temperature of from 0° C. to 30° C. to give Compound (2) (wherein R is as defined above). Preferable examples of the inert solvent to be used herein are dichloromethane, dichloroethane, acetone, pyridine, ethyl acetate, tetrahydrofuran, N,N-dimethylformamide and a mixture thereof. The acid of the acid anhydride and acid halide to be used includes acetic acid, propionic acid, benzoic acid or pyridine-carboxylic acid. Examples of the base to be used are sodium bicarbonate, sodium carbonate, potassium carbonate, triethylamine, pyridine and tributylamine.

Step (3); Compound (2) is reacted with a reagent such as phosgene dimer or phosgene trimer using a base such as pyridine in a suitable inert solvent under ice-cooling to give Compound (3) (wherein R is as defined above). The suitable inert solvent is the same as used in Step (2).

Step (4); Compound (3) is reacted in a lower alcohol at a temperature of from room temperature to 100° C. to synthesize Compound (4). The lower alcohol is the same as used in Step (1).

Step (5); Compound (4) is reacted with an acid at a temperature of from 0° C. to 30° C., and the resulting compound is reacted in the same manner as in Step (2) to give Compound (5) wherein the hydroxyl group at the 2'-position is protected (wherein R is as defined above). Examples of the acid to be used herein are hydrochloric acid, hydrobromic acid and sulfuric acid.

Step (6); Compound (5) is reacted in an inert solvent with a carboxylic acid represented by the formula: Y—$CH_2$COOH (wherein Y is as defined above) and a reagent which is usually used for forming a mixed acid anhydride, of which typical example is pivaloyl chloride, or a carboxylic acid represented by the formula: Y—$CH_2$COOH (wherein Y is as defined above) and a binder such as dicyclohexylcarbodiimide or 1-ethyl-3-(3-dimethylaminopropyl)carbodiimide hydrochloride in the presence of a base at a temperature of from −20° C. to 60° C., preferably −20° C. to room temperature, followed by reaction in the same manner as in Step (4) for removal of the protective group at the 2'-position to give Compound (6) (wherein Y is as defined above) which is a compound of the present invention. The inert solvent is the same as used in Step (2). Examples of the base to be used are pyridine, collidine, N-methylpiperidine, N-methylmorpholine, triethylamine, 4-dimethylaminopyridine and a mixture thereof.

Step (7); Compound (5) is oxidized using chromic acid, chromic acid-pyridine, pyridinium chlorochromate, pyridinium dichromate or an activated dimethyl sulfoxide in an inert solvent at a temperature of from −78° C. to 30° C., and then the resulting 3-ketone derivative is treated in the same manner as in Step (4) for removal of the protective group at the 2'-position to give Compound (7) which is a compound of the present invention. The inert solvent is the same as used in Step (2), and examples of the activating agent for dimethyl sulfoxide are acetic anhydride, trifluoroacetic anhydride, oxalyl chloride, phosphorus pentachloride, pyridinium sulfate, pyridinium trifluoroacetate, dicyclohexylcarbodiimide and 1-ethyl-3-(3-dimethyl-aminopropyl) carbodiimide hydrochloride.

Step (8); 9-Dihydroxyerythromycin A is protected at the 2'-position in the same manner as in Step (2), and reacted with a reagent such as N,N'-carbonyldiimidazole or di-2-pyridyl carbonate, and a base such as sodium hydride in a suitable inert solvent at a temperature of from −20° C. to 30° C., preferably −5° C. to 10° C. to give Compound (3). The inert solvent is the same as used in Step (2).

The compounds of the present invention have a strong antibacterial activity against not only Gram-positive bacteria but also Gram-negative bacteria, examples of which are Staphylococcus genus (*S. aureus, S. epidermidis,* etc.), Enterococcus genus (*E. faecalis,* etc.), and Haemophilus genus (*H. influenzae,* etc.).

The compounds of the present invention can be administered orally or parenterally in the various preparation forms for the purpose of the application based on the pharmacological properties. The pharmaceutical composition of the present invention can be prepared by homogeneously mixing an effective amount of the compound of the present invention in the form of a free or an acid addition salt with a pharmaceutically acceptable carrier, which may be various forms according to the desired dosage forms. Examples of the dosage forms in the present invention are tablets, capsules, powders, troches, ointments, suspensions and solutions, all of which can be prepared according to conventional preparation techniques.

The preferable dose of the compound of the present invention is from 10 to 1000 mg/day for oral administration, and 5 to 500 mg/day for parenteral administration, preferably given in a single dose or 2 to 3 divided doses per day. This dose can be increased or decreased depending on the age, body weight and conditions of the patient.

BEST MODE FOR CARRYING OUT THE INVENTION

The present invention is illustrated in more detail by the following Examples.

EXAMPLE 1

Synthesis of 9-dihydroerythromycin A 6,9;11,12-dicyclic Carbonate (1) To a solution of 20.3 g (27 mmoles) of erythromycin A 11,12-cyclic carbonate in 200 ml of methanol was added 5.0 g (0.13 mole) of sodium borohydride under ice-cooling, followed by stirring under ice-cooling for 4 hours. A further 1.5 g (0.04 mole) of sodium borohydride was added, the mixture was stirred for an hour. After the reaction, the mixture was neutralized with 2N aqueous hydrochloric acid solution, and after addition of distilled water, extracted with ethyl acetate. The organic layer was washed with an aqueous sodium chloride solution and dried over anhydrous magnesium sulfate. After evaporation of the solvent under reduced pressure, purification by silica gel column chromatography (chloroform:methanol:aqueous ammonia=15:1:0.1) gave 18.9 g (yield: 93%) of 9-dihydroerythromycin A 11,12-cyclic carbonate.

Mass(FAB) m/z: 762 [MH]$^+$ $^1$H-NMR (500MHz, CDCl$_3$) δ(ppm): 5.00 (dd, 1H, J=9.2, 3.1Hz, H-13), 4.92 (s, 1H, H-11), 3.40 (brs, 1H, H-9), 3.29 (s, 3H, 3"-OMe), 2.31 (s, 6H, NMe$_2$)

$^{13}$C-NMR (125MHz, CDCl$_3$) δ(ppm): 175.7 (C1), 153.9 (11,12-carbonate), 79.4 (C9), 49.4 (3"-OMe), 40.3 (NMe$_2$).

(2) To a solution of 10.5 g (0.14 mole) of the compound obtained in the above (1) in 100 ml of acetone was added 1.6 ml (0.17 mole) of acetic anhydride, followed by stirring for 5 hours. After the reaction, the solvent was evaporated, a saturated aqueous sodium bicarbonate solution was added, and the mixture was extracted with ethyl acetate. The organic layer was washed with an aqueous sodium chloride solution, and dried over anhydrous magnesium sulfate. Evaporation of the solvent under reduced pressure gave 10.1 g of 2'-O-acetyl-9-dihydroerythromycin A 11,12-cyclic carbonate.

Mass(FAB) m/z: 804 [MH]$^+$ (3) To a solution of 8.46 g (10.5 mmoles) of the compound obtained in the above (2) in 80 ml of pyridine was added dropwise 3.8 ml (31.7 mmoles) of trichloromethyl chloroformate diluted with 40 ml of dichloromethane under ice-cooling over a period of 30 minutes, and the temperature was gradually raised, followed by stirring at room temperature for 21 hours.

After the reaction, ice-pieces and a saturated aqueous sodium chloride solution were successively added under ice-cooling, and the mixture was extracted with dichloromethane. The organic layer was dried over anhydrous magnesium sulfate, and the solvent was evaporated under reduced pressure to give 8.65 g of the residue, a solution of which in 170 ml of methanol was then stirred at room temperature for 23 hours. After the reaction, the solvent was evaporated, and purification by silica gel column chromatography (chloroform:methanol:aqueous ammonia= 15:1:0.1) gave 4.14 g (yield: 50%) of the title compound.

Mass(FAB) m/z: 788 [MH]$^+$ $^1$H-NMR (500MHz, CDCl$_3$) δ(ppm): 5.05 (dd, 1H, J=10.4, 2.4Hz, H-13), 4.68 (s, 1H, H-11), 3.99–3.94 (m, 2H, H-9 and H-5"), 3.29 (s, 3H, 3"-OMe), 2.29 (s, 6H, NMe$_2$).

$^{13}$C-NMR (125MHz, CDCl$_3$) δ(ppm): 175.1 (C1), 153.4 (11,12-carbonate), 150.9 (6,9-carbonate), 85.5 (C9), 49.3 (3"-OMe), 40.2 (NMe$_2$).

EXAMPLE 2

Alternative Syntheses of 9-dihydroerythromycin A 6,9;11,12-dicyclic Carbonate (First Method)

To a solution of 12.3 g (14.8 mmoles) of the compound obtained in Example 1 (2) in 250 ml of pyridine was added dropwise a solution of 8.8 g (29.7 mmoles) of triphosgene in 90 ml of dichloromethane under ice-cooling over a period of 40 minutes, and the temperature was gradually raised, followed by stirring at room temperature for 18.5 hours. After the reaction, deacetylation at the 2'-position was carried out in the same manner as in Example 1(3) to give 4.53 g (yield: 39%) of the title compound.

(Second Method)

To a solution of 1.17 g (1.51 mmoles) of 2'-O-acetyl-9-dihydroerythromycin A in 20 ml of a mixture of N,N- dimethylformamide—tetrahydrofuran (mixture rate=1:1) were successively added 0.30 g (7.5 mmoles) of sodium hydride and 1.22 g (7.5 mmoles) of N,N'-carbonyl-diimidazole under ice-cooling, followed by stirring under ice-cooling for an hour. After the reaction, deacetylation at the 2'-position was carried out in the same manner as in Example 1(3) to give 0.49 g (yield: 41%) of the title compound.

EXAMPLE 3

Synthesis of 3-0-(3-pyridyl)-acetyl-5-O-desosaminyl-9-dihydroerythronolide A 6,9;11,12-dicyclic Carbonate (1) A solution of 4.53 g (5.75 mmoles) of the compound obtained in Example 1 (3) in 100 ml of 1N aqueous hydrochloric acid solution was stirred at room temperature for 15 hours, and then 2N aqueous sodium hydroxide solution and water were added thereto, followed by extraction with chloroform. The organic layer was dried over anhydrous magnesium sulfate, the solvent was evaporated under reduced pressure, and crystallization from 2-propanol gave 2.34 g (yield: 65%) of 5-O-desosaminyl-9-dihydroerythronolide A 6,9;11,12-dicyclic carbonate.

Mass(FAB) m/z: 630 [MH]$^+$ $^1$H-NMR (500 MHz, CDCl$_3$) δ(ppm): 5.13 (dd, 1H, J=10.7, 2.8Hz, H-13), 4.62 (s, 1H, H-11), 4.05 (dd, 1H, J=5.5, 3.1Hz, H-9), 2.26 (s, 6H, NMe$_2$)

$^{13}$C-NMR (125MHz, CDCl$_3$) δ(ppm): 174.4 (C1), 153.5 (11,12-carbonate), 151.1 (6,9-carbonate), 78.1 (C3), 40.2 (NMe$_2$).

(2) 2.34 g (3.7 mmoles) of the compound obtained in the above (1) was acetylated in the same manner as in Example 1(2) to give 2.46 g of 2'-O-acetyl-5-O-desosaminyl-9-dihydroerythronolide A 6,9;11,12-dicyclic carbonate.

(3) To a solution of 1.9 g (10.9 mmoles) of 3-pyridylacetic acid hydrochloride in 20 ml of dichloromethane was added 3.1 ml (22.3 mmoles) of triethylamine, and the mixture was stirred at room temperature for 30 minutes. To the mixture cooled to −15° C. was added dropwise 1.3 ml (11.0 mmoles) of pivaloyl chloride diluted with 14 ml of dichloromethane over a period of 10 minutes. After stirring for 10 minutes, to the mixture was added dropwise a solution of 2.46 g of the compound obtained in the above (2) in 30 ml of dichloromethane, and then 0.22 g (1.80 mmoles) of 4-dimethylaminopyridine was added thereto. The temperature was gradually raised, followed by stirring at room temperature overnight. After the reaction, the mixture was adjusted to pH 10 with 2N aqueous sodium hydroxide solution, and extracted with chloroform. The organic layer was dried over anhydrous magnesium sulfate, and evaporation of the solvent under reduced pressure gave 6.60 g of a foam substance, a solution of which in 70 ml of methanol was heated under reflux for 2 hours. After the reaction, the solvent was evaporated, and purification by silica gel column chromatography (acetone:n-hexane:triethylamine=30:10:0.2) and recrystallization from 2-propanol gave 1.843 g (yield: 67%) of the title compound.

Mass(FAB) m/z: 749 [MH]$^+$ $^1$H-NMR (500MHz, CDCl$_3$) δ(ppm): 5.33 (d, 1H, J=11.0Hz, H-3), 5.12 (dd, 1H, J=11.0, 2.4Hz, H-13), 4.63 (s, 1H, H-11), 4.01 (dd, 1H, J=7.3, 3.1Hz, H-9), 3.73 and 3.69 (each d, each 1H, J=15.9Hz, —OCOC<u>H</u>$_2$C$_5$H$_4$N), 2.27 (s, 6H, NMe$_2$).

$^{13}$C-NMR (125MHz, CDCl3) δ(ppm); 172.9 (C1), 153.3 (11,12-carbonate), 150.7 (6,9-carbonate), 78.6 (C3), 40.2 (NMe$_2$), 38.5 (—OCO<u>C</u>H$_2$C$_5$H$_4$N).

EXAMPLE 4

Synthesis of 3-deoxy-3-oxo-5-O-desosaminyl-9-dihydroerythronolide A 6,9;11,12-dicyclic Carbonate A solution of 0.33 ml (3.78 mmoles) of oxalyl chloride in 5 ml of dichloromethane was cooled to −78° C., and 0.54 ml (7.61 mmoles) of dimethyl sulfoxide diluted with 5 ml of dichloromethane was added dropwise thereto over a period of 10 minutes. The mixture was stirred for 20 minutes, and then a solution of 511 mg (0.76 mmole) of the compound obtained in Example 3(2) in 10 ml of methylene chloride was added dropwise thereto over a period of 10 minutes. The mixture was stirred at −78° C. for an hour, 1.9 ml (13.6 mmoles) of triethylamine was added dropwise thereto over a period of 5 minutes, and then the temperature was gradually raised to room temperature. After the reaction, distilled water was added to the mixture, followed by extraction with dichloromethane. The organic layer was dried over anhydrous magnesium sulfate, and evaporation of the solvent under reduced pressure gave 0.59 g of the residue, a solution of which in 12 ml of methanol was then stirred at room temperature for 17 hours. After the reaction, the solvent was evaporated, and purification by silica gel column chromatography (chloroform:methanol:aqueous ammonia= 15:1:0.1) gave 0.23 g of a mixture containing the title compound, which was then crystallized from 2-propanol/methylene chloride to give 10 mg of the title compound.

Mass(FAB) m/z: 628 [MH]$^+$ $^1$H-NMR (500 MHz, CDCl$_3$) δ(ppm): 5.08 (dd, 1H, J=9.8, 3.1Hz, H-13), 4.63 (s, 1H, H-11), 3.98 (dd, 1H, J=9.5, 2.1Hz, H-9), 2.27 (s, 6H, NMe$_2$).

$^{13}$C-NMR (125MHz, CDCl$_3$) δ(ppm): 203.4 (C3), 168.3 (C1), 153.0 (11,12-carbonate), 150.1 (6,9-carbonate), 40.2 (NMe$_2$).

EXAMPLE 5

Synthesis of 3-O-(2-pyridyl)-acetyl-5-O-desosaminyl-9-dihydroerythronolide A 6,9;11,12-dicyclic Carbonate Carrying out the same reaction as in Example 3(3) using 0.12 g (0.69 mmole) of 2-pyridylacetic acid hydrochloride and 0.16 g of the compound obtained in Example 3(2), there was obtained 139 mg (yield:78%) of the title compound.

Mass(FAB) m/z: 749 [MH]$^+$ $^1$H-NMR (500MHz, CDCl$_3$) δ(ppm): 5.32 (d, 1H, J=11.0Hz, H-3), 5.11 (dd, 1H, J=10.3, 2.4Hz, H-13), 4.63(s, 1H, H-11), 4.00 (dd, 1H, J=7.3, 3.1Hz; -9), 3.94 and 3.89 (each d, each 1H, J=15.9Hz, —OCOC<u>H</u>$_2$C$_5$H$_4$N), 2.29 (s, 6H, NMe$_2$).

$^{13}$C-NMR (125MHZ, CDCl$_3$) δ(ppm): 173.1 (C1), 153.4 (11,12-carbonate), 150.8 (6,9-carbonate), 78.5 (C3), 43.8 (—OCO<u>C</u>H$_2$C$_5$H$_4$N), 40.3 (NMe$_2$).

EXAMPLE 6

Synthesis of 3-O-(N-benzyloxy-carbonyl) aminoacetyl-5-O-desosaminyl-9-dihydroerythronolide A 6,9;11,12-dicyclic Carbonate To a solution of 1.63 g (2.4 mmoles) of the compound obtained in Example 3(2) in 34 ml of dichloromethane were successively added 1.34 g (6.4 mmoles) of N-Cbz-glycine, 1.23 g (6.4 mmoles) of 1-ethyl-3-(3-dimethylaminopropyl)

carbodiimide hydrochloride and 0.13 g (1.1 mmoles) of 4-dimethylaminopyridine under ice-cooling, followed by stirring under ice-cooling for 2.5 hours. After the reaction, a saturated aqueous sodium bicarbonate solution was added, and the mixture was extracted with chloroform. The organic layer was dried over anhydrous magnesium sulfate, and evaporation of the solvent under reduced pressure gave 3.53 g of the residue, a solution of which in 40 ml of methanol was then stirred at room temperature overnight. After the reaction, the solvent was evaporated, and purification by silica gel column chromatography (chloroform:methanol:aqueous ammonia=20:1:0.1) gave 1.95 g (yield;98%) of the title compound.

Mass(FAB) m/z: 821 [MH]$^+$ $^1$H-NMR (500MHz, CDCl$_3$) δ(ppm): 5.35 (d, 1H, J=11.0Hz, H-3), 5.15–5.09 (m, 3H, H-13 and —NHCO$_2$CH$_2$Ph), 4.62 (s, 1H, H-11), 4.21 and 3.90 (each dd, each 1H, —OCOCH$_2$NH—), 4.02 (dd, 1H, J=7.3, 3.1Hz, H-9), 2.24 (s, 6H, NMe$_2$).

$^{13}$C-NMR (125MHz, CDCl3) δ(ppm): 172.9 (C1), 153.3 (11,12-carbonate), 150.8 (6,9-carbonate), 79.3 (C3), 67.0 (—NHCO$_2$CH$_2$Ph), 42.9 (—OCOCH$_2$NH—), 40.2 (NMe$_2$).

EXAMPLE 7

Synthesis of 3-O-aminoacetyl-5-O-desosaminyl-9-dihydroerythronolide A 6,9;11,12-dicyclic Carbonate To a solution of 1.95 g (2.4 mmoles) of the compound obtained in Example 6 in 20 ml of methanol was added 10% palladium carbon catalyst, followed by stirring under ordinary pressure and hydrogen overnight. After the reaction, the catalyst was removed by Celite filtration, and the filtrate was evaporated under reduced pressure to give 1.81 g of the title compound.

Mass(FAB) m/z: 687 [MH]$^+$ $^1$H-NMR (500MHz, DMSO-d$_6$) δ(ppm): 5.08 (d, 1H, J=11.1Hz, H-3), 5.02 (dd, 1H, J=10.7, 2.6Hz, H-13), 4.39 (s, 1H, H-11), 4.10 (dd, 1H, J=5.6, 3.0Hz, H-9), 3.99 (d, 1H, J=7.2Hz, H-1'), 3.91 and 3.86 (each d, each 1H, J=17.9Hz, —OCOCH$_2$NH$_2$).

$^{13}$C-NMR (125MHz, DMSO-d$_6$) δ(ppm): 173.3 (C1), 169.7 (—OCOCH$_2$NH$_2$), 152.9 (11,12-carbonate), 150.6 (6,9-carbonate), 103.0 (C1').

EXAMPLE 8

Syntheses of 3-O-(N-4-quinolylmethyl)aminoacetyl-5-O-desosaminyl-9-dihydroerythronolide A 6,9;11,12-dicyclic Carbonate (Compound A) and 3-O-[N,N-bis(4-guinolylmethyl)]aminoacetyl-5-O-desosaminyl-9-dihydroerythronolide A 6,9;11,12-dicyclic Carbonate (Compound B)

To a solution of 1.81 g of the compound obtained in Example 7 in 20 ml of methanol were added 1.0 g (6.4 mmoles) of 4-quinoline-carboxyaldehyde and 0.7 ml (13 mmoles) of acetic acid, followed by addition of 0.5 g (8.0 mmoles) of sodium cyanoborohydride under ice-cooling, and the mixture was stirred for 4 hours. After the reaction, the mixture was adjusted to pH 10 with 2N aqueous sodium hydroxide solution, extracted with ethyl acetate, and washed with a saturated aqueous sodium chloride solution. The organic layer was dried over anhydrous magnesium sulfate, and the solvent was evaporated under reduced pressure, followed by purification by silica gel column chromatography (chloroform:methanol:aqueous ammonia=15:1:0.1) to give 0.66 g (yield; 34%) of 3-O-(N-4-quinolylmethyl)-aminoacetyl-5-O-desosaminyl-9-dihydroerythronolide A 6,9;11,12-dicyclic carbonate (Compound A) and 0.04 g (yield; 2%) of 3-O-[N,N-bis(4-quinolylmethyl)]-aminoacetyl-5-O-desoisaminyl-9-dihydroerythronolide A 6,9;11,12-dicyclic carbonate (Compound B).

(Compound A)

Mass(FAB) m/z: 828 [MH]$^+$ $^1$H-NMR (500MHz, CDCl$_3$) δ(ppm): 5.41 (d, 1H, J=11.0Hz, H-3), 5.15 (dd, 1H, J=10.7, 2.4Hz, H-13), 4.64 (s, 1H, H-11), 4.41 and 4.26 (each d, each 1H, J=14.3Hz, NHCH$_2$-quinoline), 4.03 (dd, 1H, J=7.0, 2.8Hz, H-9), 3.97 (d, 1H, J=7.0Hz, H-1'), 3.88 (d, 1H, J=4.6Hz, H-5), 3.63 and 3.56 (each d, each 1H, J=17.4Hz, —OCOCH$_2$NH$_2$), 2.14 (s, 6H, NMe$_2$).

$^{13}$C-NMR (125MHz, CDCl$_3$) δ(ppm): 173.0 (C1), 153.3 (11,12-carbonate), 150.8 (6,9-carbonate), 104.3 (C1'), 40.2 (NMe$_2$).

(Compound B)

Mass(FAB) m/z: 969 [MH]$^+$ $^1$H-NMR (500MHz, CDCl$_3$) δ(ppm): 5.42 (d, 1H, J=10.4Hz, H-3), 5.14 (dd, 1H, J=10.4, 2.4Hz, H-13), 4.62 (s, 1H, H-11), 4.53 and. 4.35 (each d, each 2H, J=14.0Hz, —N(CH$_2$-quinoline)$_2$), 4.02 (dd, 1H, J=7.3, 3.1Hz, H-9), 3.76 (d, 1H, J=7.3Hz, H-1'), 3.78 (d, 1H, J=4.9Hz, H-5), 3.63 and 3.49 (each d, each 1H, J=17.7Hz, —OCOCH$_2$NH—), 2.09 (s, 6H, NMe$_2$).

$^{13}$C-NMR (125MHz, CDCl$_3$) δ(ppm): 173.1 (C1), 153.3 (11,12-carbonate), 150.8 (6,9-carbonate), 40.2 (NMe$_2$).

EXAMPLE 9

:Synthesis of 3-O-(N-methyl-N-4-quinolylmethyl) aminoacetyl-5-O-desosaminyl-9-dihydroerythronolide A 6,9;11,12-dicyclic Carbonate To a solution of 0.48 g (0.58 mmole) of 3-O-(N-4-quinolylmethyl)aminoacetyl-5-O-desosaminyl-9-dihydroerythronolide A 6,9;11,12-dicyclic carbonate (Compound A) obtained in Example 8 in 10 ml of methanol were added 0.28 ml (3.5 mmoles) of 37% aqueous formaldehyde solution and 0.40 ml (7.0 mmoles) of acetic acid, followed by addition of 0.26 g (4.1 mmoles) of sodium cyanoborohydride under ice-cooling, and the mixture was stirred for 4 hours. After the reaction, the mixture was adjusted to pH 10 with 2N aqueous sodium hydroxide solution, extracted with ethyl acetate, and washed with a saturated aqueous sodium chloride solution. The organic layer was dried over anhydrous magnesium sulfate, and the solvent was evaporated under reduced pressure, followed by purification by silica gel column chromatography (chloroform:methanol:aqueous ammonia =20:1:0.1) to give 0.33 g (yield; 68%) of the title compound.

Mass(FAB) m/z: 842 [MH]$^+$ $^1$H-NMR (500MHz, CDCl$_3$) δ(ppm): 5.40 (d, 1H, J=11.0Hz, H-3), 5.15 (dd, 1H, J=11.0, 2.4Hz, H-13), 4.64 (s, 1H, H-11), 4.30 and 4.16 (each d, each 1H, J=14.0Hz, —NMeCH$_2$-quinoline), 4.02 (dd, 1H, J=7.3, 3.1Hz, H-9), 3.49 and 3.42 (each d, each 1H, J=17.1Hz, —OCOCH$_2$NMe—), 2.50 (s, 3H, NMe), 2.14 (s, 6H, NMe$_2$).

$^{13}$C-NMR (125MHz, CDCl$_3$) δ(ppm): 173.0 (C1), 153.3 (11,12-carbonate), 150.7 (6,9-carbonate), 77.8 (C3), 57.5 (—OCOCH$_2$NMeCH$_2$-quinoline), 42.6 (NMe), 40.1 (NMe$_2$).

Experiment [In Vitro Antibacterial Activity]

The in vitro antibacterial activity of the compound obtained in Example 3 as an example of the compound of the present invention against various experimental bacteria was measured using sensitive disc media (produced by Eiken Chemical Co.) according to the MIC measuring method specified by the Japan Society of Chemotherapy. Azithromycin was used as a comparative drug. The results are expressed as MIC value (Minimum Inhibitory Concentration, μg/ml), and shown in Table 1. The compound obtained in Example 3 showed to have a strong antibacterial activity, in particular, against *Haemophilus influenzae*.

TABLE 1

|  | Compound | |
| --- | --- | --- |
| Microorganism | Comparative drug | The compound obtained in Example 3 |
| *S. aureus* 209P-JC | 0.39 | 0.10 |
| *S. aureus* Smith 4 | 0.39 | 0.10 |
| *S. epidermidis* IID 866 | 0.20 | 0.10 |
| *E. faecalis* CSJ 1212 | 1.56 | 0.10 |
| *S. aureus* J-109 | >100 | >100 |
| *S. aureus* B1 | >100 | 0.20 |
| *H. influenzae* ATCC 19418 | 3.13 | 1.56 |
| *H. influenzae* ATCC 33533 | 1.56 | 0.78 |
| *H. influenzae* ATCC 43095 | 1.56 | 0.78 |

Industrial Utilization

The compounds of the present invention have a strong antibacterial activity against Gram-positive bacteria and Gram-negative bacteria. Therefore, the compounds of the present invention are useful as antibacterial agents for the treatment of bacterially infectious diseases in human beings and animals (including farm animals).

We claim:

1. An erythromycin A derivative represented by the formula (I):

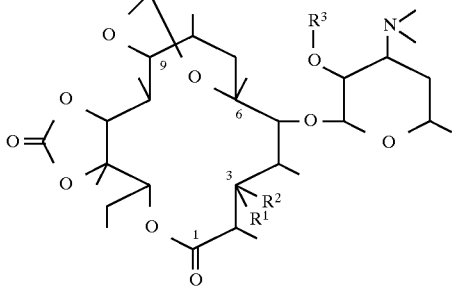

wherein $R^1$ is a group represented by the formula: —OCOCH$_2$Y, wherein Y is a pyridyl group, a quinolyl group, a p-nitrophenyl group or a group represented by the formula: —NR$^4$R$^5$ wherein $R^4$ and $R^5$ may be the same or different, and are each a hydrogen atom, a methyl group, a pyridylmethyl group, a quinolylmethyl group or a benzyloxycarbonyl group; or a cladinosyloxy group; $R^2$ is a hydrogen atom; or $R^1$ and $R^2$ together form an oxo group; $R^3$ is a hydrogen atom, an acetyl group, an ethylsuccinyl group or a nicotinoyl group; or a pharmaceutically acceptable salt thereof.

2. A pharmaceutical composition comprising an effective amount of the erythromycin A derivative or the pharmaceutically acceptable salt thereof according to claim 1 and a pharmaceutically acceptable carrier.

3. An antibacterial preparation comprising the erythromycin A derivative or the pharmaceutically acceptable salt thereof according to claim 1 as an effective component.

4. A method for the treatment of a bacterially infectious disease which comprises administering a pharmaceutically effective amount of the erythromycin A derivative or the pharmaceutically acceptable salt thereof according to claim 1 to a patient.

* * * * *